US008571884B2

(12) United States Patent
Badgett et al.

(10) Patent No.: US 8,571,884 B2
(45) Date of Patent: Oct. 29, 2013

(54) HEALTHCARE COMMUNICATION AND WORKFLOW MANAGEMENT SYSTEM AND METHOD

(75) Inventors: Becky Badgett, Goodlettsville, TN (US); Jeremy Rodgers, Goodlettsville, TN (US); Lee Smith, Goodlettsville, TN (US); Curt Freemyer, Goodlettsville, TN (US)

(73) Assignee: Aionex, Inc., Goodlettsville, TN (US)

( * ) Notice: Subject to any disclaimer, the term of this patent is extended or adjusted under 35 U.S.C. 154(b) by 431 days.

(21) Appl. No.: 12/139,307

(22) Filed: Jun. 13, 2008

(65) Prior Publication Data

US 2009/0313046 A1    Dec. 17, 2009

(51) Int. Cl.
*G06Q 10/00*    (2012.01)
*G06Q 50/00*    (2012.01)

(52) U.S. Cl.
USPC .................................................. 705/2; 705/3

(58) Field of Classification Search
USPC ......................................................... 705/2, 3
See application file for complete search history.

(56) References Cited

U.S. PATENT DOCUMENTS

| 6,598,119 | B2 * | 7/2003 | Becker et al. ................. 711/119 |
| 7,212,987 | B2 * | 5/2007 | Swanke et al. ............... 705/7.15 |
| 2002/0013716 | A1 * | 1/2002 | Dunham et al. ................... 705/2 |
| 2003/0074222 | A1 * | 4/2003 | Rosow et al. ..................... 705/2 |
| 2006/0049936 | A1 * | 3/2006 | Collins et al. ............ 340/539.11 |
| 2006/0143044 | A1 * | 6/2006 | Conry et al. ...................... 705/2 |
| 2007/0194939 | A1 * | 8/2007 | Alvarez et al. ............. 340/573.1 |
| 2008/0071578 | A1 * | 3/2008 | Herz et al. ........................ 705/3 |

* cited by examiner

*Primary Examiner* — Neha Patel
(74) *Attorney, Agent, or Firm* — Stephen H. Hall; Jeremy A. Smith; Bradley Arant Boult Cummings LLP

(57) ABSTRACT

A communication and workflow management system and method is provided for integrating a wide range of health care organization workflow management functions, generated by automated systems, manual and automated events associated with patients and staff interactions, through input-output devices such that requests and dispatch requests can be handled locally or over a widely distributed network, and can be tracked and escalated as required. The invention features a rules engine and database that identifies and defines resources, patients, tasks, and task handling. The invention uses extensive logic for the assignment of tasks and communication with resources that can execute tasks, tracking, completion of task, and escalation of tasks. The communication system can be integrated with staff and equipment tracking for automated closure of tasks.

11 Claims, 7 Drawing Sheets

HEALTHCARE COMMUNICATION AND WORKFLOW MANAGEMENT SYSTEM AND METHOD

BACKGROUND OF THE INVENTION

This invention generally relates to a healthcare communication and workflow management system and method. In particular, the invention relates to a system and method for integrating a wide range of health care organization workflow management functions, generated by automated systems, manual and automated events associated with patients and staff interactions through input-output devices such that requests and dispatch requests can be handled locally or over a widely distributed network, and can be tracked and escalated as required.

Both patients and staff in healthcare facilities need voice communications. Traditionally, patient communications have been answered at the local nursing station down the hall, using patient/nurse call systems. Unfortunately, this often leads to long wait times and inefficient handling of many requests. For example, if a patient needs housekeeping or dietary services, an overloaded nurse may take quite some time to respond to the request. Most previous systems have limited the healthcare communications system problem to a strictly defined topology involving patient/nurse call communications systems hard-wired to local nursing stations.

In general, patient/nurse call systems allow patients to activate a "call" button or pick up a phone handset located in their room to contact a nurse or staff member at the nursing station located down the hall. The call button or phone handset normally triggers an audio connection between the patient's room and the nurse's station, whereupon the patient can speak directly with a nurse at the nurse station. Most patient/nurse call systems also allow input connections for emergency signaling devices, for example Bath Emergency Stations, Shower Stations, Hallway Indicator Lights, Code Blue Stations, Patient Beds and Call Cord devices. These patient room peripherals are also configured to notify the nurse's station serving the particular patient when activated.

The patient bed or the patient themselves may also be connected to a number of monitoring devices which can also communicate information directly to the nurses' station, for example, bed monitoring devices such as "brakes on", mattress firmness, incontinence, patient presence, and patient weight. Physiological devices may also be used, for example, heart rate monitors, breathing monitors, patient temperature sensors, blood pressure monitors, EKG monitors, ventilators, and IV pumps. Other miscellaneous devices and/or monitors may also be present, for example, treatment and therapy devices that administer medication. Information from these systems may not only be displayed at a nurse station, but may also be configured to trigger an alarm or action item at the nurse station under certain conditions, for example if a patient's temperature gets to high.

In most prior art systems, the patient/nurse call system was hard wired directly to the single, local nurse station serving the particular patient location. Such a system had an extremely minimal ability to track and document patient requests. These systems lacked any capability to dispatch non-nursing personnel to a patient, or to dispatch other personnel to handle non-patient duties such as cleaning a room, repairing a bed, or doing preventative maintenance on a piece of equipment. Moreover, some existing systems will not directly route patient calls to a nurse. Thus, facilities have to staff the nurse station with sufficient personnel to respond to all patient calls. Unfortunately, many of the patient calls are unrelated to medical care or medical questions. By initially directing all patient calls, regardless of their nature, to the nurse station serving the patient location, nurses are often consumed with answering and responding to patient calls when other staff personnel could properly respond to the patient request. For example, a patient request for assistance walking to the bathroom could be answered by non-medical staff rather than a nurse. Even if the nurse does not have to perform the specific task, it has taken the nurse time to answer the call and locate or communicate with the appropriate personnel to respond. Moreover, there is little or no documentation of the request.

Research has shown that the response time to answer a patient call in this fashion averages about 1 minute. This is often due to the fact that nursing staff are busy responding to other patient calls that could be handled by other hospital personnel. Once received, the process of relaying the purpose of the patient call received at the nurse station to the appropriate person for response was to (a) seek and find the necessary caregiver; (b) seek and page the necessary caregiver; or (c) seek and tell someone else. Research also shows that the average time to complete a particular communication event in this manner is 1.8 minutes. Again, in these circumstances, there was little or no documentation of the event.

The traditional method for responding to emergency situations was also inefficient. Often, when an emergency situation developed, for example when a patient monitor detected a dangerous heart rhythm, the process of communicating the emergency code required numerous phone calls, encrypted paging, and overhead paging. These communication events were also often not documented.

Studies have also shown that patients recover faster when their surroundings are quiet and peaceful. Unfortunately, prior art systems that send nurse calls to the local nursing station or directly to the nurse are loud, and often include ringing phones, overhead pages, and nurses talking at volumes that can be heard by patients.

In addition to voice communications, additional information related to patient care must be communicated to facility staff. For example, information from emergency signaling devices, bed monitoring devices, and physiological devices must be efficiently communicated to the proper personnel. In addition, a medical facility must utilize systems to manage requests for patient transport, package management, requests for the food service department, maintenance work orders, bed management, pharmacy requests, and lab requests, just to name a few. These systems, however, are often separate computer systems that are not integrated into a facility's overall information system and do not provide efficient communication with the proper staff. Moreover, these systems do not provide adequate or real time tracking and logging of activity data, nor do they permit escalation of task requests.

With regard to patient transport, nursing traditionally performs all transfers and discharges by department. The standard process is for a nurse to seek and find a wheelchair, and transport patient from unit to unit or for discharge. This process can average over thirty minutes.

With regard to package management, traditionally a facility's package delivery system was either performed by an outside third party courier service or by the employee with the need.

With regard to the food service department, the following process is traditionally initiated to order and deliver a tray to a new admit or late tray request. The patient's doctor would write the diet order. The order was entered into the facility database by a secretary. The order would print in the food services office and a diet clerk would pull the order off the printer. The diet clerk would document any changes on a diet sheet and complete a meal ticket. The dietary clerk would then place the meal ticket in the window of the diet office. A dietary aide would pull the ticket and prepare the tray. The aide would then deliver the tray to the nursing station and the nurse would deliver to the patient.

With regard to maintenance work orders, the following process describes the general communication process performed from beginning of a maintenance work order assignment through completion. A request is received by phone/facsimile/relay through an employee at the facility operations office window. Depending on the priority or nature of the request, the request was either: (a) entered into the work order system for immediate printing and dispatch via a 2-way radio; (b) entered into a work order system for immediate printing and given to a supervisor once located; or (c) entered into the work order system for printing during the next day's routine printing. Depending on which action was chosen, a technician either (a) responded to radio dispatch, recording and procuring parts as needed in the facility operations storeroom completing the work order documentation upon return; (b) supervisor dispatched work order verbally, by page, by radio, or by overhead page, then continued as stated above after dispatch; or (c) received work order in bulk during the next morning, completing as stated above. The final communication step was completion of work orders with parts list documentation entered into the system by office and parts room staff. Research shows that the average response time to communicate a work order process from assignment to conclusion was approximately 30 minutes.

With regard to bed management, communication events seeking to admit a patient to a facility generally followed the following process. The ER, Operating Room or doctor's office phoned the Admitting Office for rooms STAT or based on unit census, the need became STAT. The communication event was routed as follows: The STAT call for room request was generated through the Admitting Office. The Admitting Office called housekeeping to clean a room. The housekeeping office would page the housekeeping supervisor and waited on a return call. After speaking with the housekeeping supervisor, the supervisor would page an aide to clean a room or actually walk the floors with an aide to find a specific room to begin cleaning. The supervisor would communicate this information to the housekeeping office. Usually the aide would return the page to the supervisor notifying of a specific room being cleaned. The housekeeping supervisor would call and notify the Admitting Office. The Admitting Office would then notify the requesting party of the actual room location. The final action was the Admitting clerk entering the patient data into the facility information system network. Research has shown this process averages twenty minutes.

With regard to lab requests, the traditional process of order entry involved nursing personnel entering lab orders into the facility information network (normally the clinical applications therein). The notification process regarding STAT/NOW orders involved paging or calling the Lab Tech, and would interrupt the Lab Tech working on pending orders.

With regard to pharmacy requests, the traditional process of order entry involved nursing personnel entering pharmacy orders into the facility information network (normally the clinical applications therein). The notification process regarding pharmacy orders involved paging or calling the pharmacy, and would interrupt the pharmacy Tech working on pending orders.

Prior patents that address healthcare communications systems focus on nurse call from a specific physical bed to a local nursing station, rather than permitting arbitrary relationships among patients, in beds on the nursing unit or elsewhere, equipment, and staff functions both local and in arbitrary geographic locations. In general, they deal with hierarchical, relatively stable relationships rather than dynamic tasking. Others dealing with patient telemetry do not take an integrated view of the room environment of the patient, or associate patient physiological information shown to staff with administrative and historical knowledge of the patient. The obvious drawbacks of the prior art systems and methods include inefficient communication of orders and tasks, lack of order and task assignment, lack of tracking and escalation, and lack of proper documentation.

Applicant's present invention overcomes the drawbacks and limitations in the prior art systems and methods and offers health care facilities a more efficient, secure, and patient oriented healthcare communication system and method capable of managing and supporting the services fundamental to a modern health care organization.

SUMMARY OF THE INVENTION

The present invention recognizes and addresses various of the foregoing limitations and drawbacks, and others, concerning proper utilization of hospital staff, and intelligent routing of staff requests. Therefore, the present invention is directed to healthcare communication and workflow management system and method that utilizes intelligent dispersal of certain information, especially tasking, to specific personnel to properly allocate staff to their most efficient use, and allows tracking, escalation, and documentation of requests.

One aspect of the present invention features a rules engine and database comprising a rules processing implementation with supporting data structures that enables the creation of applications incorporating a new, highly efficient methodology for health care provision. The rules engine and database is fundamentally a system by which best practices are captured as rules which, while directly editable and interpretable by human operators, wholly define the behavior of systems implemented with the rules engine and database as a foundation. Multiple instances of the rules engine and database can be instantiated to implement a system, communicating with each other via a proprietary protocol defined below. Applications developed with the rules engine and database as a foundation can be tailored by system installers and end users to implement desired behaviors specific to individual organizations. This new approach successfully mitigates long wait times and inefficient request handling attributes of previous applications attempting to address this problem space. For example, under competing system architectures, if a patient needs housekeeping or dietary services, an overloaded nurse assigned to the patient may take quite some time to respond to the request.

In one aspect, the invention comprises a set of resources, personnel, orderings, data tables, human interfaces, and machine-to-machine interfaces required to meet a goal of functionality that is of clinical, hospitality, and system administrative functions.

In another aspect, unlike the prior art systems, the present invention does not treat requests as "pipelines", but as having complex branching and cooperative concurrency. It is parallel in execution nature, and supports cooperative processing across multiple instances of the rules engine spanning multiple computing devices.

In another aspect, the invention provides a rules engine and database that identifies and defines resources, patients, tasks, and task handling in a hospital environment, for example, what resources to which tasks can be assigned. The rules engine and database forms part of the facility's overall facility information network. The rules engine database uses extensive logic for assignment of tasks and communicating with resources that can execute the tasks (task dispatching), tracking the completion of tasks (task tracking), and escalating to roles or people when the original resource for completion is not available, the task is incomplete, or the task request goes unanswered (task escalation). Task and resource logging are integrated, along with access control, both to be HIPAA compliant and to provide information on process and financial efficiency.

In another aspect, the present invention also may accept task or order requests (and completion events) from any number of "inputs", including human input devices, automated scripts, and timers.

The present invention further offers secure data handling meeting requirements of, at a minimum, the Health Insurance Portability and Accessibility Act (HIPAA) Security and Privacy rules, the auditability requirements of clinical trials governed by 21CFR11, and the electronic prescribing rules of the Office of Diversion Control of the Drug Enforcement Administration.

The present invention further provides methods for storing data hierarchically (i.e., top level has all data) or using federated principles (i.e., different places have parts of the total information, the parts located through a secure directory). In either case, the data storage is fault-tolerant, and synchronized to a query-able relational database for long term storage, analysis, and reporting.

The present invention further provides a consistent interfacing technique for accepting messages and event indications from a variety of standard and proprietary information systems used for healthcare and emergency services.

The invention also has the capability to integrate hospital-specific demographic information, as from locally developed or third-party admission systems, into data about the patient and the patient's room. This capability also includes external reservation of beds by associated healthcare facilities, doctors, and emergency service agencies.

The invention also allows for creation of a set of roles and capabilities for staffers, and securely associating both specific people with roles, as well as those people present or on-call at a specific time. The definitions here are both hierarchical (e.g., a registered nurse can do the tasks of a nursing technician, but not vice versa) and nonhierarchical (e.g., one registered nurse on a unit may be designated as the medication dispensing or intravenous monitoring person, even though other nurses are capable of this function).

The invention also provides for task handling involving rules for escalating resource requests that have not been satisfied when a timer expires, with an extensive capability for defining exception conditions and their handling. Generally, a request will normally have another level of escalation, until it stops at the CEO of a facility if all other efforts have failed. In some cases, an escalation request may even bring in external services.

The present invention further provides for opportunistic task scheduling, in which the system recognizes that a given task cannot be completed until some event (i.e., as different from a time or date) takes place, such as a hospital bed must be vacant before certain cleaning or maintenance actions on it.

The present invention further provides methods for abstracting a bed and a patient to a location, such that data flow can follow a patient in transport or otherwise away from the assigned room.

The present invention further provides efficient tracking and communication with both equipment and personnel resources.

The present invention provides an extensible method for defining healthcare organizations, their subordinate organizations, and policies appropriate to each organizational level.

In one aspect, the present invention enables the collection of data from disparate sources, enables long term storage, enables the provision of mechanisms for data review and presentation, and directly applies that data to govern the flow of associated processes as appropriate.

In another aspect, the present invention provides the ability to track and document patient requests, various tasks and orders, and emergencies situations.

In another aspect, the present invention provides mechanisms that direct tasks, and communicates information, to appropriate personnel, thus providing a more efficient allocation of resources and distribution of information.

In another aspect, the present invention provides an organizational-wide solution for immediate, private, and non-disruptive dispersal of tailored information to the parties to have a role to play in a particular event or task.

Additional objects and advantages of the invention are set forth in, or will be apparent to those of ordinary skill in the art from, the detailed description as follows. Also, it should be further appreciated that modifications and variations to the specifically illustrated and discussed features and materials hereof may be practiced in various embodiments and uses of this invention without departing from the spirit and scope thereof, by virtue of present reference thereto. Such variations may include, but are not limited to, substitutions of the equivalent means, features, and materials for those shown or discussed, and the functional or positional reversal of various parts, features, or the like.

Still further, it is to be understood that different embodiments, as well as different presently preferred embodiments, of this invention, may include various combinations or configurations of presently disclosed features, elements, or their equivalents (including combinations of features or configurations thereof not expressly shown in the figures or stated in the detailed description).

These and other features, aspects and advantages of the present invention will become better understood with reference to the following descriptions and appended claims. The accompanying drawings, which are incorporated in and constitute a part of this specification, illustrate an embodiment of the invention and, together with the descriptions, serve to explain the principles of the invention.

In one exemplary embodiment, a variety of sources of task requirements, mechanisms to assign resources to tasks, to track performance of tasks, and to combine tasks into workflows, are interconnected via a data network. At the core of the network are a group of rules engine and database instances, recognizing task-related events, and applying rules based both on best healthcare practices and facility-specific policies. When a certain event occurs, for example, a bed monitoring device signals an incontinence event, a signal is routed through the network to a rules engine and database instance which is aware of information about the patient associated with the event through a database interface. This rules engine and database instance determines the nature of the event, and generates a task for a local nurse serving that patient to go see the patient. Because this organization has configured its rule set to call for it, the attending nurse is notified of the event through a text pager via the rules engine and database's communication interfaces. If the task is not closed promptly, the rules engine and database's executing rules generate additional reminders to see the patient. If the patient is not attended to in some predetermined amount of time, additional personnel can be contacted, i.e., the call escalated.

In another exemplary embodiment, an event stimulus can be intelligently routed to multiple parties that need to know the information. For example, if a heart rate monitor drops too low, the rules engine and database can direct communication to, for example, the local nurse station, a specific nurse, and an on-site cardiologist. The system allows automatic logging and auditing of the requests, communication events, and responses for auditing purposes.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
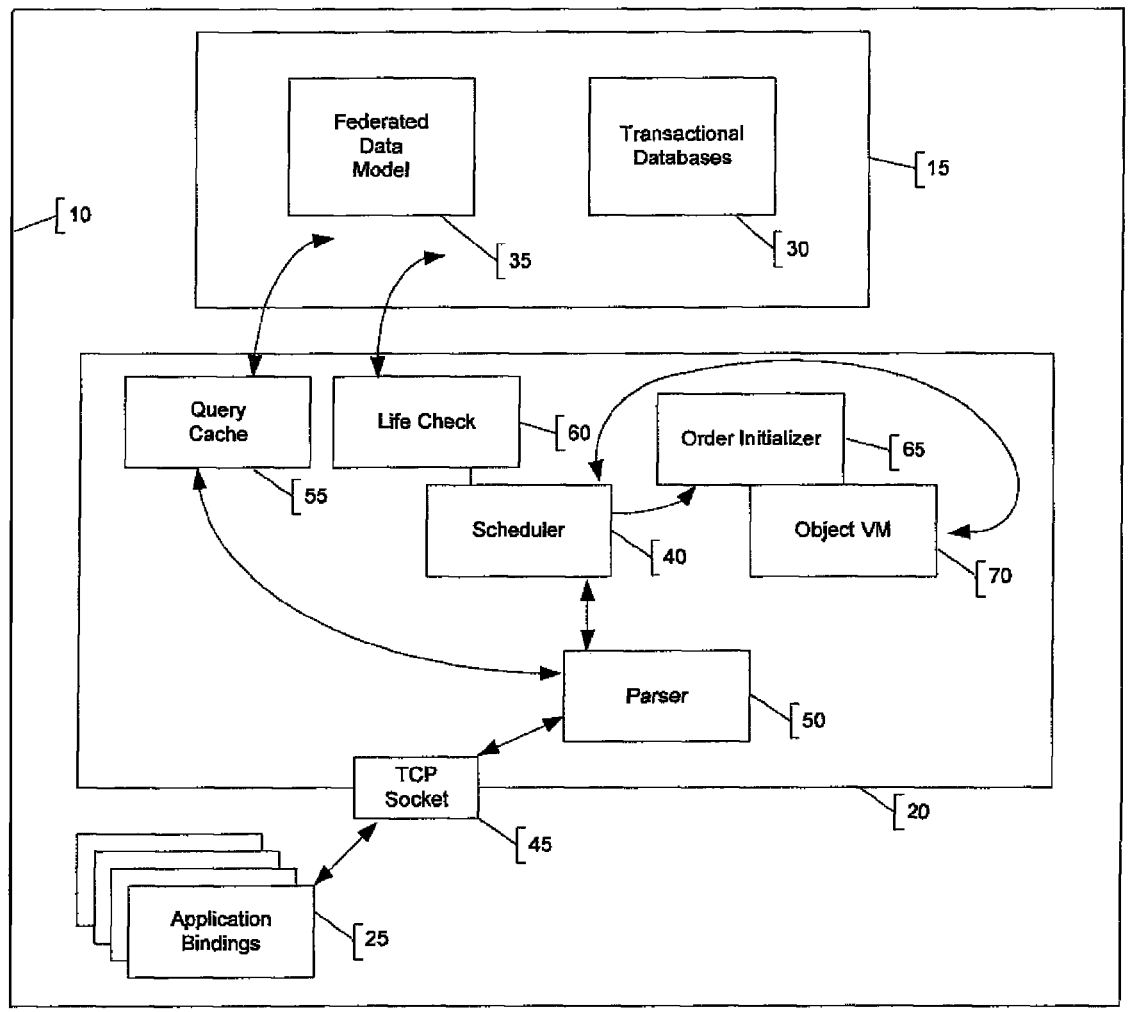
FIG. 1 depicts an overview of one exemplary embodiment of one aspect of the invention.

Repeated use of reference characters throughout the present specification and appended drawings is intended to represent the same or analogous features or elements of the invention.

DETAILED DESCRIPTION OF THE PREFERRED EMBODIMENTS

Reference will now be made in detail to presently preferred embodiments of the invention, examples of which are represented in the accompanying drawings. Such examples are provided by way of an explanation of the invention, not limitation thereof. In fact, it will be apparent to those skilled in the art that various modifications and variations can be made in the present invention, without departing from the spirit and scope thereof. For instance, features illustrated or described as part of one embodiment can be used on another embodiment to yield a still further embodiment. Still further, variations in selection of materials and/or characteristics may be practiced, to satisfy particular desired user criteria. Thus, it is intended that the present invention cover such modifications and variations as come within the scope of the present features and their equivalents.

As disclosed above, the present invention is particularly concerned with an improved, healthcare communication and workflow management system and method that allocates hospital resources and staff to maximize their efficiency. To best understand the present invention and its various embodiments, the following terms have the following definitions.

"Resources" are things the system manages, and that are in varying states of being available and/or assigned to a task, i.e., allocated. Resources include (a) physical resources such as a bed, a wheelchair, or a portable clinical instrument such as an EKG or X-ray, and (b) human or people resources, either as individuals available for assignment or for future scheduling. The granularity of a people resource can be a specific individual, a role, or a team. Person and role are subclasses of resource.

"Staffer" is a human resource who works for a particular organization. From an identity management standpoint, it is necessary to define individual staffers and their credentials; from a task dispatching standpoint, it is necessary to define skills associated with individuals.

"Tasks" are actions that need to be taken.

"Requester" is a person requesting or entering a task. A requester may be a patient or a staffer.

FIG. 1 depicts an overview of one exemplary embodiment of one aspect of the invention. In the exemplary embodiment depicted in FIG. 1, the healthcare communication and workflow management system 10, can be broadly broken down into three discrete parts, the database 15, the rules engine 20, and application bindings 25. Within the database 15, this embodiment comprises a transactional database 30 and a federated data model 35. The transactional database 30 stores stateful data about the communication system 10, and provides long-term and permanent storage of data for auditing and reporting. Rules, discussed further below, reside in the transactional database 30 at start up.

The federated data model 35 may store data about the current state of the communication system 10, and the current processes being implemented. One advantage of utilizing a transactional database 30 along with a federated data model 35 is the more efficient utilization of the communication system 10 resources. By accessing the federated data model 35 for certain "current" data, the communication system 10 avoids having to continually access the transactional database 30 for all needed data. Prior art systems traditionally utilize just a transactional database 30, without the use of a federated data model 35. In these systems, the applications poll the transactional database 30 for changes in data. However, polling a traditional database in this manner can be inefficient, due in part to the fact that these transactional database have to be "searched" for the proper data. Accessing current information from a federated data model 35 may thus streamline data acquisition and use.

For example, the communication system 10 may have data stored that patient John Doe is in room 235. This information may be available in both the transactional database 30 and the federated data model 35. The federated data model 35 and transactional database 30 may also include data about the patient's current body temperature, for example 98.6 degrees. However, older data about patient John Doe, for example his body temperature two hours ago, or two days ago, would preferably be stored only in the transactional database 30. By pushing certain changes in data to the federated data model 35, certain recent information about properties that are being tracked by the system are more accessible and less calls to the transactional database 30 needed.

It will be appreciated by those of skill in the art that the use of a federated data model 35 is not required, but is simply a more efficient way to manage current data.

Referring to FIG. 1, application bindings 25 refers to applications that utilize the rules engine 20 and database 15 for task assignment, order initialization, and tracking, for example, a nursing module, a bed management module, a dietary services module, laboratory dispatch module, pharmacy module, operating room module, emergency room module, etc. As depicted in FIG. 1, these application bindings 25 may interface with, and utilize, the rules engine 20 and database 15, for task assignment and tracking. Application bindings 25 are often run on the facility's information network, and are available to applicable staffers through workstations (often PCs) in the staffers' work area. For example, a nursing module will traditionally be available to nurses at the nursing station, a pharmacy module available to pharmacists in the pharmacy, etc. In other situations, all various applications may be available at a workstation, with access to specific applications (i.e., nursing, pharmacy, etc.) controlled by passwords or other security measures.

Referring to FIG. 1, the rules engine 20 can contain various functionality, and may comprise the features and functionality set forth in FIG. 1. In FIG. 1, the application bindings 25 communicate with the rules engine 20 through a communication interface. The communications interface may be a TCP socket 45 as depicted in FIG. 1, although other standard interfaces known in the industry may be substituted. For information routed from the application bindings 25 to the TCP socket 45 or from the TCP socket 45 to the application bindings 25, the information may also be passed through a parser 50.

The parser 50, is preferably implemented partially in LUA space, or other interpretive language, and partially in C++ space (or other compiled object oriented language producing native machine code), enabling rule provisioning without recompilation of the C++ rules engine itself. It should be recognized that further references to LUA are not limitations, and that other interpretive, virtual machine based language executed in a sandbox, but with bindings to functions implemented in compiled language space may be used. Data sent to or received by the rules engine 20 is preferably formatted as XML messages with a binary header prepended to them. In this embodiment, the header may consist of a start character (ASCII character 134) followed by a 4 byte integer representing the message length, which is then followed by another 4 byte integer representing a sequence number. An exemplary embodiment, for illustration purposes only, is set forth below:

```
struct HeaderDefinition
{
unsigned char startChar;
unsigned int msgLen;
unsigned int seqNum;
} __attribute__((packed));
```

In this embodiment, when an external message is received, for example from an application binding 25, by the rules engine 20 via TCP Socket 45, it is parsed for a <command> tag, i.e., does a situation exist necessary to create a rule. A command tag can itself be a rule or a triggering condition. If the command tag is present, the rules engine 20 will preferably respond with an acknowledgement, or ACK, to the parser 50. If the command tag is not present, a non-acknowledgement, or NACK, may be sent.

In this embodiment, the ACK/NACK structure may be comprised of the header as defined above (with the sequence number set as sent to the rules engine 20) followed by an ASCII character "1" for ACK or "0" for a NACK.

In this embodiment, once the verification has taken place and the ACK/NACK returned, parsing of the rest of the message will proceed. The parser 50 extracts the <command> payload and performs work accordingly. In this embodiment, the rules engine 20, in its minimal configuration, may support at least three core commands via the LUA portion of the parser 50:

1. Query—requiring as parameters: a <sql> tag pair containing the sql query to be issued and a <cache> tag pair representing whether or not to have the rules engine 20 cache the result set to the query cache 55 (discussed below). A cached result may expire after some set time period, for example, after 60 seconds. This will return a result set for the query to be parsed by an XML parser.

2. Createorder—requiring as parameters: tag pairs for each of the order object elements, for example rule and serviceid, although more elements can be utilized. This may return the created order id to the requestor (via, for example, the workstation) in an XML message similar to the database query.

3. Modifyorder—requiring as parameters: tag pairs for each of the order object elements, for example the order id (i.e., a unique identifier, normally indexed sequentially), although more elements can be utilized. If the order id exists, specified elements will be updated, with the exception of "rule" and "ordered" elements.

Additional commands are easily implemented as extensions to this core functionality.

The scheduler 40 is generally responsible for initiating and governing the execution of the various "orders" (transactions), allowing them to yield for external stimulus and then be reactivated when that stimulus has occurred. This can be thought of as a "sleep on condition" as implemented by high-level languages.

The scheduler 40 preferably contains a list of rules applicable for particular orders. For any particular "order," one or more rules may be executed. For example, an "order" may be to notify a physician that a particular elderly patient has exited their bed, thereby tripping a bed exist sensor (i.e., the "trigger condition"). The following pseudocode illustrates a rule implementing an exemplary response. The rule responds to the trigger condition by calling another named rule by directly triggering it (i.e., no further condition needs to be met):

RULE BEDEXIT_CONDITION: IF [BEDEXIT==TRUE] THEN CALL RULE BEDEXIT WITH PARAMETERS ROOM, PATIENT, ADDENDING_PHYSICIAN, TRIGGER_TIME

Bedexit rule, which is directly triggered by the conditional example:

RULE BEDEXIT: IF [DIRECTLY TRIGGERED] THEN
    CALL RULE NOTIFY WITH PARAMETERS ROOM, PATIENT, ATTENDING_PHYSICIAN, TRIGGER_TIME
    CALL RULE WRITE_LOG_FILE WITH PARAMETERS ROOM, PATIENT, ATTENDING_PHYSICIAN, TRIGGER_TIME
    CALL RULE UPDATE_PATIENT_STATUS_DISPLAY WITH PARAMETERS ROOM, PATIENT, TRIGGER_TIME
    CALL RULE UPDATE_PHYSICIAN ALLOCATIONS WITH PARAMETERS ATTENDING_PHYSICIAN, TRIGGER_TIME
    CALL RULE ESCALATION_WATCHDOG WITH PARAMETERS ATTENDING_PHYSICIAN, TRIGGER_TIME, RETRIGGER_INTERVAL=10 MINUTES

In this example, the data provided to the application rule as parameters is passed down to other rules as they are referenced by the initial rules that trigger them. In this example, the rule accesses the contextual data directly, rather than to directly query the database or object model by way of facilities exposed by the scheduler 40. In this example, the notification rule will not talk directly to a paging terminal, nor will the log file writer talk directly to a disk subsystem. They will simply update data in the database and/or object model, which will create a condition triggering other components to respond. These components may be rules, or they may be applications.

The rules may be provided two utility functions to coordinate behavior with the scheduler 40: RegisterEvent( ) and WaitForEvents( ). For example, some rules may require completion of a preceding rule before it initiates. This allows serialized processing of information.

The scheduler 40 determines whether the input constitutes some type of trigger condition necessary for execution of rules, and directs when to start and stop the execution of rules. If the necessary trigger condition exists, it sends the necessary information for execution of the rules to the order initializer 65 (discussed below).

Referring to FIG. 1, the rules engine 20 may also include an order intializer 65. The order initalizer preferably exists in LUA space, or other interpretive language, and is responsible for configuring the LUA virtual machine ("VM") 70 with a ruleset as appropriate for the given serviceid. The current ruleset is preferably cached in memory (i.e., the physical RAM of the rules engine host hardware) and can be reloaded by sending a HUP signal to the rules engine process. This instructs the rules engine 20 to reload the ruleset from the database. Any existing orders (transactions) will be executed with the ruleset as it existed when they were instantiated. This feature is key to allowing the rule engine 20 to be field-upgraded without disrupting rule processing. Once the ruleset is loaded, a LUA table is constructed, preloaded with the events to be executed. This table can be self-modified by the events/tasks to provide polymorphism so that the rule can dynamically reconfigure itself in response to any defined condition. Every step through this table will increment the "ipindex" for the given order. The "ipindex" can be thought of as an instruction pointer. This schema allows execution of a rule to be resumed at the point of failure in the event of catastrophic failures of rules engines, to include both hardware and software failures. Once the order execution environment is fully initialized, the rule begins its execution until it yields by either suspending itself with the scheduler 40 or by fully completing execution.

In the embodiment shown in FIG. 1, the LUA utility bindings (not depicted) form a component of the rules engine 20 and database 15 schema. They are a set of utility extension functions provided to the rules to allow them to interact with the database and other components of the rules engine and database architecture outside of LUA space. The catalog of utility functions can be extended arbitrarily, allowing the rules engine and database's functionality to be expanded to support new applications.

The rules engine 20 may include a redundancy/fault tolerant application, depicted in FIG. 1 as Lifecheck 60. Lifecheck 60 may be used to ensure proper execution of rules. For example, multiple rules engines 20 could be utilized for a communication system 10. In one configuration, a single rules engine 20 could be used for two or more application bindings 25. In another configuration, a single rules engine 20 could be used for a single application binding 25. If there are multiple rules engines 20 that are working together, they will preferably share the federated data model 35 and transactional databases 30.

Lifecheck 60, preferably implemented in C++ space (or other compiled object oriented language producing native machine code), updates a status table in the common database to allow any other concurrently running rules engines to be coordinated. If any rule engine fails to report within a parametrically defined threshold, its orders are reassigned to the engine that first detected the failure condition. This engine assumes responsibility for the orders and reinstantiates them locally. Before the resurrected orders begin execution, the ipindex for each order is advanced to the last-known-good state reached prior to the failure. Execution of the pending orders then resumes. The failure is handled transparently from the perspective of the requesting client.

For example, if a particular order has five rules associated with it, and a particular rules engine 20 fails after only completing three of the rules, the Lifecheck 60 will detect that the rules engine 20 failed, communicate with the transactional database 30 and/or the federated data model 35 to determine that rules one through three were completed, and request that an alternative rules engine 20 complete rules four and five. Thus, Lifecheck 60 provides a fault-tolerant mechanism to ensure continuous availability of data and communication even if there is some failure within a particular rules engine 20.

Referring to FIG. 1, the rules engine 20 may also contain a query cache 55, preferably implemented in C++ space (or other compiled object oriented language producing native machine code). When a database query is made through the rules engine via the "query" utility function discussed above, the result set can be optionally cached or recovered from a cache. Query cache hits relieve the database 15 and TCP infrastructure of load. If the <cache> flag is set to 1, the cache will be searched prior to a database query being attempted. If a result set is found for the corresponding query it is immediately returned to the caller. If a matching result set is not present, the query is issued to the database 15, the result set is formatted as an XML message, the message is cached and then returned to the caller. For example, if a patient ID of #123456 is provided and the patient name needed, the first time that information is retrieved from the database 15, it may be stored in the query cache 55 for some pre-determined period of time. If the same patient ID is provided and the patient name again needed, within the pre-determined amount of time, it can obtain that information from the query cache 55. Again, this reduces the amount of processing required by the database 15.

The rules engine 20 may also include an Order Execution Environment Manager (OEEM) (not depicted), which may be implemented as a C++ thread (or other compiled object oriented language producing native machine code). In one embodiment, the OEEM has two primary responsibilities. The first primary responsibility is the replenishment of a pool of uninitialized order execution environments (LUA VMs). When the scheduler 40 must instantiate new orders, it begins that process by harvesting an execution environment from the uninitialized order pool. This allows the rules engine 15 and database 20 architecture to defer the overhead of on-demand VM sandbox creation by sacrificing memory, this mitigating the performance impact on executing rules. When an order completes execution, the execution environment is released, reducing the number of available environments in the uninitialized order pool. Normally, the pool is replenished during idle time, eliminating the impact of this activity on rule processing. If the order pool depletes during an activity surge, new order environments will be created on-demand until demand wanes and the order pool is restocked. The other primary OEEM task is to garbage collect any orders that have completed but were not cleaned up by the scheduler 40. This condition does not nominally occur, but the mitigating functionality exists to prevent the rules engine 20 from leaking resources in unforeseen circumstances.

In one embodiment, the query cache 55 and Lifecheck 60 operate in a C++ solution space (or other compiled object oriented language producing native machine code), while the order initializer 65 and object VM 70 run in an interpretive language solution space, preferably LUA. The scheduler 40 preferably has aspects of both. By using an interpretive language solution space to implement the rules, a new rule can be dynamically added for the specific facility without having to recompile and redeploy the entire system.

Figure 2:
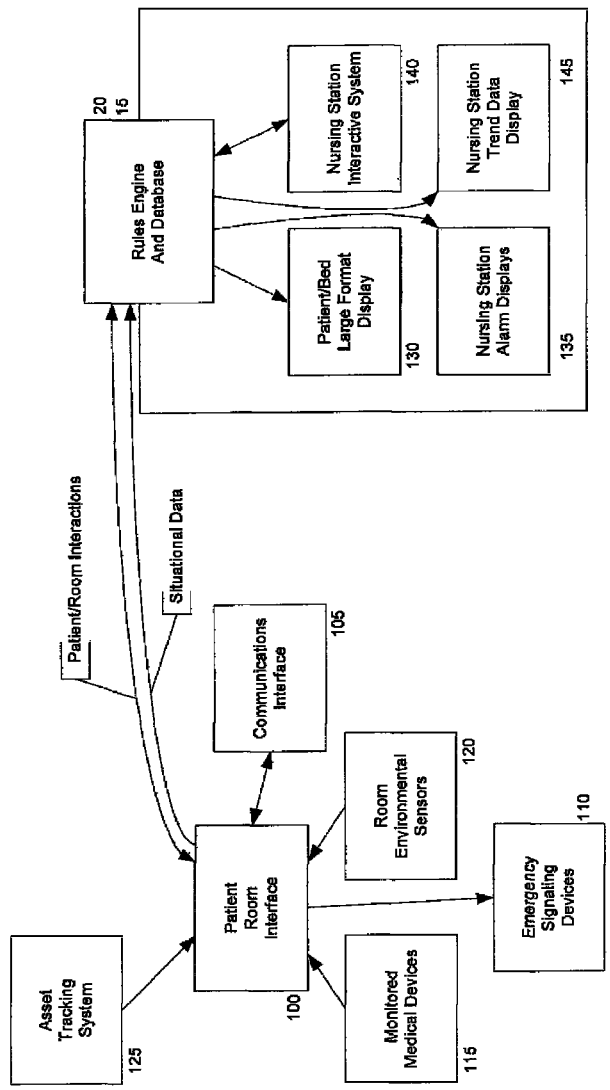
FIG. 2 illustrates one embodiment of the invention deployed for room/patient monitoring and communication system for nursing applications.

FIG. 2 depicts an exemplary embodiment of how the rules engine 20 and rules engine database 15 can be deployed. Referring to FIG. 2, a patient room may contain one or more of the following: a patient room interface 100, a communications interface 105, emergency signaling devices 110, monitored medical devices 115, and room environmental sensors 120. The patient room interface 100 acts as the interface between the patient room and the rules engine 20 and database 15, and acts as a data acquisition point.

The communications interface 105 may be any suitable device known in the industry, for example, a nurse call button connected to a unit mounted on the headwall of the patient room, or a basic telephone handset. The emergency signaling devices 110 could be, for example, Bath Emergency Stations, Shower Stations, Hallway Indicator Lights, Code Blue Stations, and Call Cord devices. Monitored medical devices 115 could be bed monitoring devices (for example, "brakes on", mattress firmness, incontinence, patient presence, and patient weight), physiological devices (for example, heart rate monitors, breathing monitors, patient temperature sensors, blood pressure monitors, EKG monitors, ventilators, and IV pumps), and miscellaneous other devices and/or monitors pertinent to patient care. Room environmental sensors 120 could include, for example, room temperature monitors. Other miscellaneous other devices and/or monitors may also be present, for example, treatment and therapy devices that administer medication.

The communications interface 105, monitored medical devices 115, emergency signaling devices 110, and room environmental sensors 120 are preferably in communication with the patient room interface 100. The patient room interface 100 preferably converts audio signals from the communications interface 105 to digital signals for transmission. The patient room interface 100 also preferably converts data received from the other devices and sensors to digital signals for transmission. In turn, the patient room interface 100, is in communication with the rules engine 20 and database 15.

The patient room interface 100 may also be in communication with a facility asset tracking system 125. The asset tracking system 125 may monitor and track the location of various "assets" of a facility, and may include personnel and equipment. For example, nursing staff may wear wireless devices that transmit signals that can be detected to determine their presence in a particular location, i.e., a patient room. Similarly, assets, for example a wheelchair, can also have tracking devices on them so that their location can be tracked and monitored.

Still referring to FIG. 2, the rules engine 20 and database 15 may be in communication with a number of different systems. In FIG. 2, the rules engine 20 and database 15 may be in communication with a patient/bed large format display 130, nursing station alarm displays 135, nursing station interactive system 140, and a nursing station trend data display 145. In this embodiment, the patient/bed large format display 130 may be an overview of various patients, provided via a workstation, that may be accessible for a wide range of facility personnel, from nurses to facility executives. The information provided is normally "top level" information, and is not designed to provide detailed information. For example, a facility CEO may want to know how many patient beds are occupied at any one time.

The nursing station alarm displays 135 may provide a nursing station monitoring a specific patient with any alarms or emergencies, via a workstation or other device, detected by the monitored medical devices 115, emergency signaling devices 110, and/or room environmental sensors 120. The nursing station trend data display 145 may provide a nursing station, via a workstation or other device, with long term data being provided by monitored medical devices 115 and room environmental devices 120, for example, allow the nurse to view the heart rate of a patient over the last two hours. The nursing station interactive system 140 may provide the nursing station audio communication with a patient room and/or control over certain room environmental sensors 120 in the patient's room.

Thus, as discussed above, if a monitored medical device 115 detects that a patient has exited the bed (and thus tripped the bed exit sensor), that data will be transmitted via the patient room interface 100 to the rules engine 20 and database 15 for processing. Depending on the rules for a specific facility, appropriate rules will be executed. Moreover, notification may be provided as appropriate, for example, at the nursing station alarm displays 135 in this example.

In another example, if a monitored medical device 115 reaches a pre-determined threshold, a trigger is activated (for example, the heart monitor drops below a defined threshold). The trigger signal is sent to the patient room interface 100, through the computer network, and to the rules engine 20 and database 15. Depending on the rules set forth in the rules engine 20, a task is generated, and resources identified and contacted. In the heart monitor example, the task may be routed to a nursing station alarm displays 135. Preferably, the patient information and monitoring information is displayed on the workstation in the applicable nursing station. The trigger may also generate an additional task, with resources identified and contacted. For example, in the heart monitor example, a task for a trend analysis on the heart monitor could be ordered to determine if the patient's heart rate drops every time he/she takes medication.

Figure 3:
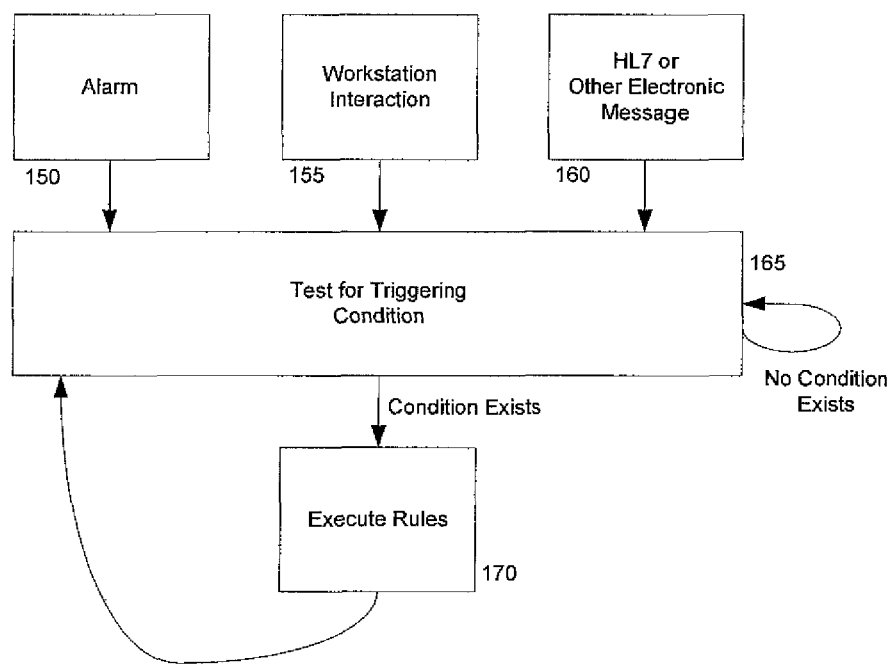
FIG. 3 illustrates exemplary embodiments of stimulus that can be used to trigger and/or influence the processing of rules by the present invention.

Depicted in FIG. 3 are exemplary examples of stimulus that can trigger and/or influence the processing of rules by the rules engine 20. For example, an alarm 150 from an emergency signaling devices 110 (i.e., actuation of a call or code call button), or a signal from a monitored medical device 115 can act as the stimulus that can trigger or influence the processing of a rule by the rule engine 20. Such stimulus is generally referred to herein as a "Trigger" or "Triggering Condition". Triggers can be also be generated through some workstation interaction 155, i.e., medical personnel manually entering information in a workstation, for example, that a patient has entered the operating room. A Trigger can also be generated by HL7 or other message 160, for example through an interface with another clinical system. For example, a Trigger could be activated by a clerk utilizing the facility's admissions module to register that a patient has been assigned to a particular bed. Triggers may also be automatically generated by the system, for example when a predefined amount of time expiring from a prior task not being responded to (discussed further below with respect to escalation), or entry of a resource to a location where the resource is used. Once a signal is received from an alarm 150, workstation interaction 155, HL7 or other message 160, or other input, the rules engine 20 tests to see if whether such input constitutes a Trigger or Triggering Condition 165. If so, the rules engine 20 then executes the appropriate rule(s) 170.

As described herein, the rules engine 20 contains instructions that predefine (or allow the user to predefine) how each Trigger is handled, i.e., rules, governing what tasks are generated, what message is sent, how it is sent, to whom it is sent, where it is sent, how it is handled, etc. Each Trigger preferably results in the generation of one or more rules.

The database 15 may also contain information or access information about the current patients, room information, patient room peripherals, and monitoring and signaling devices. For example, the database 15 may contain information that John Doe is in Room 421, and include pertinent medical information about John Doe, for example his weight, height, medical condition, allergies, dietary requirements, and the patient room peripherals and monitoring and signaling devices that are associated with John Doe. Much of this information may be dynamically assigned when, for example, medical monitoring equipment is connected in the particular patient room (i.e., the system is configured to detect and store location and patient information when the appropriate devices are connected). Thus, when a Trigger occurs, and is routed to the rules engine 20 and database 15, the system may be configured to automatically associate the Trigger with the particular patient and any pre-defined information contained in the rules engine 20 and database 15.

As an example, if the rules engine 20 receives a Trigger from a heart monitor, the system can detect that it was from a specific room and that the patient in that room is allergic to certain heart medication. The rules engine 20 and database 15 also generate one or more tasks (for example, "immediate response required—life threatening condition"), and assigns one or more resources. Thus, the rules engine 20 and database 15 may page one or more local nurses (i.e., the available staffers), page the local cardiologist, broadcast an audio page over the facility intercom, and display the heart monitor history on various workstations, for example the nursing station alarm displays 135. The rules engine 20 and database 15 can be configured to distribute the task information and patient information to various places.

As discussed above, tasks can be automatically created by a Trigger. Tasks can also be manually input into one of the various workstations throughout the facility. For example, a patient may make a call from their room and request assistance to go the restroom. The person receiving the patient call will preferably have all pertinent information about the patient available on the workstation (provided by the rules engine and database), and may then enter an order into his/her workstation. The rules engine 20 executes the appropriate rules and assigns one or more resources to the task, and communicates the task to the appropriate personnel. In this case, it may be a text message to a clerk that handles patient assistance requests. Other examples include, a nurse requesting a transport for a patient to get an X-Ray (message to transportation clerk), a patient request for a dinner (message to Food Services), or for a nurse request to change the bed linens (message to housekeeping).

The various information distributed by the rules engine 20 and database 15 is preferably displayed in the various units and areas of the hospital through workstations, which may be personal computers. Tasks and requests can also be input and monitored through the workstations. They are preferably touch screen computers communicatively connected to the facility information system and the rules engine 20 and database 15. For example, food services, housekeeping, maintenance, admitting/discharge, lab, pharmacy, operating room, the emergency department, and the nursing stations will preferably have one or more workstations. Individual patient rooms may also have a workstation. This allows staffers to input, receive, and track tasks, and provide on-line history of the tasks and work lists. The workstations may also provide information about staffers assigned to certain tasks by title, role, and cost center. This information is preferably provided by the rules engine 20 and database 15. The workstations preferably include security parameters to limit access to certain information by certain personnel. This can be by separate log in passwords, or predefined security permissions associated with the personnel ID badges.

Tasks may also be communicated using text pagers, cell phones, or any other traditional communication devices commonly used in healthcare organizations to communicate with personnel. For facilities that employ paging transmitters and other devices used for personal communications with medical staff, these devices may be under the direct control of the rules engine 20 and rules engine database 15. This personal communications function can extend beyond hospitals into community emergency communications systems.

Another aspect of the invention relates to the various hierarchical and nonhierarchical relationships among facility personnel, and the specific roles that they have. In one aspect, the invention provides for the creation of various roles for facility personnel. For example, one common role in a health care organization is a nurse. When the system is first configured for a particular facility, and the roles defined, the superior and inferior roles may also be identified. For example, the role of nurse may include a junior nurse, basic nurse, senior nurse, and a nurse specialist. The attributes and/or roles of each role can be also defined. For example, a basic nurse could be assigned the following attributes and/or roles (i.e., respond to the following tasks): (a) able to respond to decrease in blood pressure; (b) able to respond to patient request for nurse; (c) able to respond to patient complaint about pain; (d) able to respond to bath emergency station pull cord activation.

These are only examples, and nurses would obviously be identified with numerous attributes. Other personnel, for example, physicians, dietary personnel, housekeeping, maintenance, and clerks in the facility can likewise be identified and their attributes defined. The various role names, hierarchy and attributes are preferably maintained in the rules engine 20 and database 15.

When a new person is hired, i.e., a staffer, they may be entered into the system. A personal ID may be created for the staffer. The name of the staffer is entered, and the security token may be identified. The security token is designed to allow access by the staffer only to authorized areas of the facility information network and physical locations in the facility. The staffers in a particular role may then be defined. The system may maintain a status of the staffers currently active (e.g., in the hospital or on call) within a particular role, i.e., nurses on staff, maintenance personnel on staff, dietary personnel on staff, etc. Teams may also be created that contain multiple human roles. For the rules engine 20 and database 15 to effectively allocate tasks, the system should know what staffers are available, and the skill sets they possess. This can be accomplished through a standard list of shifts, on-call status, and other means of scheduling, or facilitated by employees logging in and out, perhaps manually, or automatically by their identification tags as discussed below. Thus, the system can dynamically enter the available staffers for task assignment. Defining security tokens, attributes, and roles for staffers allows for better information flow. For example, custodial staff will not need access to the neonatal care unit or medical information of patients and will not be contacted or paged for medical questions.

Another advantage of identification of roles and staffers filling those roles is the ability to define security parameters. For example, nurses may be permitted to enter, review, and track lab orders and pharmacy requests, while this information will not be available to housekeeping or maintenance personnel. Thus, the system can be configured to provide for various "permissions" to limit access to various applications and data managed and distributed by the invention.

In order to efficiently respond to patient needs, and manage workflow in a healthcare environment, the present invention manages extensive information from various aspects of a healthcare facility and allocates that information to the appropriate personnel. For example, a typical healthcare facility may have a housekeeping department, food services department, maintenance department, admitting/discharge department, lab, pharmacy, operating room department, emergency room department, and nursing station(s). These departments are normally communicatively connected to the facility information system network. The nursing stations are also communicatively connected to the various patient rooms that they serve. Preferably, the various units and areas of the hospital each have one or more workstations, or unit PCs, which allow staff to access and input information to and from the facility information system network. As discussed herein, the invention allows efficient communication across all aspects of the facility's workflow.

Task management and assignment relies on basic schedule definitions to which human and physical resources can be assigned. The status of particular resources, such as a nurse on duty, inherits both human resource and time/assignment contexts.

Another aspect of the present invention is the ability to escalate tasks. The present invention allows reminders and for additional tasks to be generated if a task is not addressed during some predefined amount of time, i.e., escalation as further discussed below.

To assist in the escalation of tasks, the present invention may detect the presence of staffers when responding to various tasks. Most healthcare facilities have some means of monitoring facility personnel, and are well known in the art. One aspect of the invention provides for the ability to detect the presence of various facility personnel and equipment through the use of identification badges. The badges are electronic devices that transmit unique identity signals, preferably infrared or ultrasound, although other methods of transmission can be used. The badges preferably issue a signal every few seconds. The badge may associate specific information about the badge wearer, for example, the person's name, title, cost center, security permissions, and personal identification number, all preferably housed in the database 15. Badges can also be associated with and attached to equipment. When used with equipment, the badge may associate specific information about the equipment, for example, nomenclature, manufacturer, model number, serial number, asset tag number, purchase date, service date, and date of last preventative maintenance.

Signals from the badges are received by various receivers located throughout the facility, for example, in patient rooms, hallways, operating room, emergency room, etc. The various receivers detect the presence of a badge when the badge is within the range of the receiver. In one embodiment, the receivers are powered by an enclosure containing power, current limiting boards, and multiple connection ports for the receivers. Alternative embodiments for configuration of the receivers are known to those of skill in the art, for example wireless receivers. The various receivers are preferably in communication with the rules engine 20 and database 15.

ID badges can also be used in association with patients. For example, when a patient is admitted, the rules engine 20 and database 15 receives information either from institution-specific admissions (or other administrative systems), from a system that produces HL7 admission records, or, possibly at the "placeholder" level, bed reservations from affiliated hospitals, doctors, or from emergency services. A patient may be provided with an electronic ID badge that may be used to automatically detect a patient's presence in various locations. The patient's presence in a particular location may then be automatically transmitted to the database 15. This is advantageous when, for example, the patient is assigned a phone number upon admission. Thus, in one embodiment phone calls can be routed to that patient depending on the location of the patient at a particular time.

Figure 4:
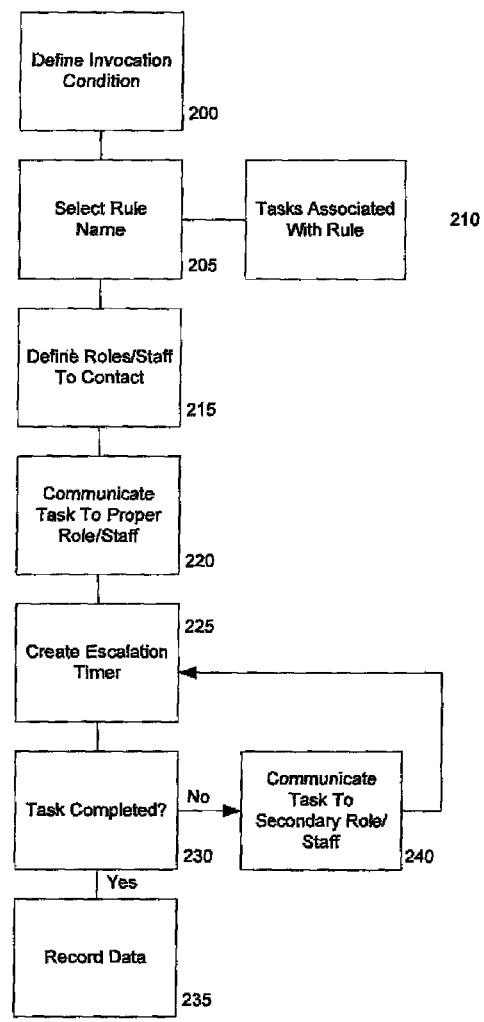
FIG. 4 illustrates one embodiment of the rules processing and escalation parameters of the invention.

Depicted in FIG. 4 is one embodiment of the various rule escalation that can be automated for applications utilizing the rules engine 20 and database 15. In one aspect, the invention provides for the creation of various escalation rules when the system is first configured, or for modifying escalation rules. In the exemplary embodiment in FIG. 4, the first step is define the "invocation condition" 200, i.e., a Trigger. For example, a heart monitor detects a drop in heart rate thus triggering a rule. A rule name is then selected 205, with each rule normally having one or more tasks associated therewith (block 210 in FIG. 4). The roles and/or staffers associated with the task, and to which the task(s) will be communicated, are defined (block 215). This may include the primary person responsible for handling the task, as well as other staffers that will be required to respond if the task is not completed in the allocated time. In block 220, the task is communicated to the proper roles and/or staffers. An escalation timer is preferably set 225, i.e., each rule should have a predefined amount of time that the user deems appropriate for the task to be responded to or completed. In block 230, the system determines whether the task is complete. If completed, the completed task is recorded in the database 15, and may include by whom the task was completed, how long it took, etc. (block 235). If the task is not completed within the allocated time, in block 240, the system communicates to the secondary roles and/or staffers (identified in block 215) and a new escalation timer set (block 225), and the process repeated. The rule may also define what the organizational/geographical resources or staffers to which the task will be communicated, each of which may have different escalation timer rules. If the task is not handled during the predefined response time, there is a defined failure procedure, i.e., escalation. In this case, the task may be communicated to additional resources (i.e., (1) expand the organizational/geographic scope, or (2) expand the range of resource types that can satisfy the request).

An example of the first parameter would be to expand the task assignment to page a nursing assistant not just on a single ward, but on a group of wards. An example of the second parameter would be to expand the task originally for a nursing assistant to include registered nurses. The escalation timer may be reset each time a task is escalated. Tasks may be defined with escalation procedures, up to the CEO if necessary, when no other solution exists to finding resources. Escalation definition may apply both to demands for human and physical resources.

For example, the invocation condition 200 could be a request to clean a room. The nurse would then select the rule on the workstation at the nurse station (step 205), which has one or more tasks associated with it (step 210), for example, contact housekeeping, log request, update room status, and start escalation timer. The rules engine 20 and database 15 selects a role associated with the rule, assigns a resource, in this case, a staffer from housekeeping (step 215). The task is then communicated to the staffer, likely by text page and a message to the housekeeping workstation (step 220), and a timer set (step 225). If the specific staffer does not respond in the prescribed time (step 230), an additional role and associated staffer can be paged (step 240), for example a housekeeping supervisor. Response to a task may be determined by the presence detection from the ID badges and receivers or by manual input into a workstation. The task can automatically be "closed" when the presence is detected, or the task can be manually "closed" by input into a workstation.

Physical resources can be defined and the various hierarchical and nonhierarchical relationships among equipment or sets of equipment contained in the rules engine 20 and database 15. For example, upon initial configuration, or later modification, the present invention can store data on physical resources in the database 15. Such data may include the name of the physical resources, define the superior and inferior physical resources, and define the attributes of a particular resource. For example, a physical resource might be a Type "I" heart monitor or Type "II" heart monitor (these are arbitrary designations). The Type "I" heart monitor may be defined to be superior to Type "II" monitors. The attributes of each would be input into the rules engine database, for example, Type "I" may be useable for adult patients and pediatric patients, while Type "II" may only be usable for adult patients.

While escalating the skill level or scope of search is more associated with human resources than physical ones, escalation still may apply for physical resources. For example, all breathing machines of a certain limited-capability type may be in use, but a policy may allow the substitution of a more capable machine if that is the only type available.

Because so much information about staff, patients, equipment, and location are converged, intelligent decisions about which staff member is most capable of handling a request can be made. For example, a patient who needs a catheter examined may be assigned to a staff member who is qualified, located nearby, and is less heavily tasked than other staff matching the criteria similarly. Thus, the present invention allows for decisions made by rules with a high degree of cognizance of the state of the hospital as a whole organism.

Figure 5:
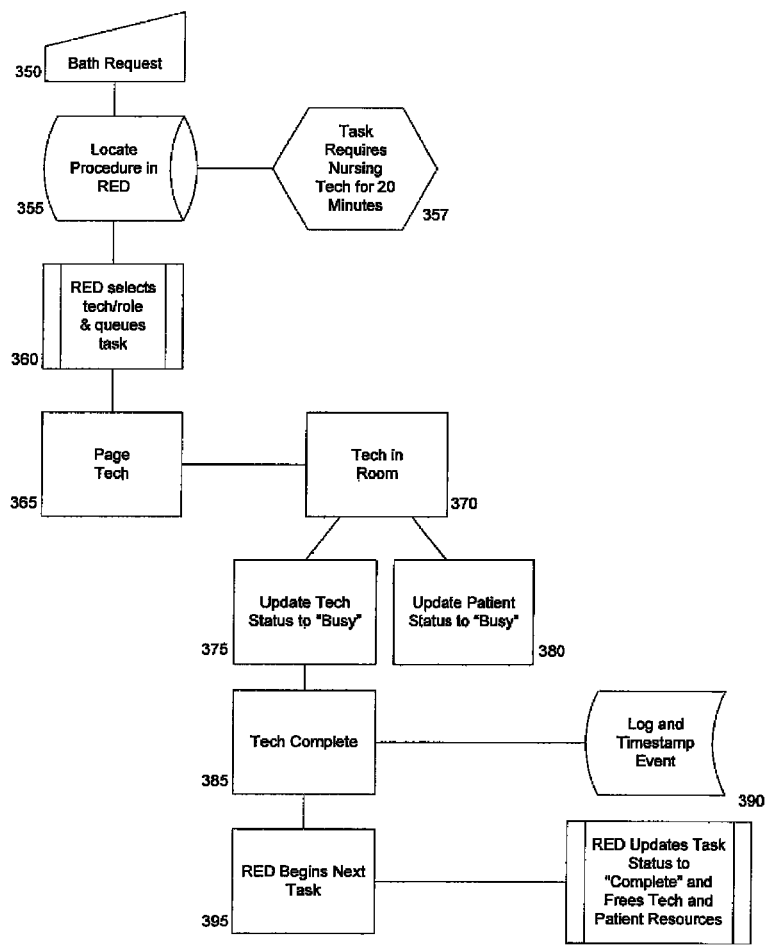
FIG. 5 illustrates one exemplary embodiment of task creation and completion.

Depicted in FIG. 5 is an exemplary creation, scheduling, and execution of a rule, requiring one or more resources. The task in FIG. 5 is associated with a patient, but could equally well be a maintenance task for hospital equipment. Note that the task in FIG. 5 affects multiple queues and status indicators, such as staff and patient. A task has a name, is associated with one or more resources (possibly in underfined/pending state), and has initiation, completion, and optional escalation rules. Tasks may be created by programmed scripts (e.g., maintenance schedules), explicit staff interaction with a workstation, as a result of significant events (e.g., a Code Blue call button), or by messages from other automated systems.

Depicted in FIG. 5 is an example bath request from a patient 350, which may be input by a nurse in a workstation at the nursing station, and an exemplary workflow of one embodiment of the invention. In this instance, the request originates from the application binding 25, specifically the nursing application. In step 355, the request goes to the rules engine 20 and database 15 for procedure lookup. In other words, the system determines whether the triggering conditions exist for execution of a rule. In this example, the rules engine 20 and database 15 outline that a nursing tech will be needed for 20 minutes 357. In FIG. 5, after the need for a nurse tech has been identified, the rules engine 20 selects the specific nurse tech/role, and queues the task 360. The specific nurse tech is then paged 365 (preferably by text pager), and the nurse tech goes to the patient's room. After the task is communicated to the appropriate personnel, the rule may "go to sleep" as long as the escalation timer does not expire. The presence of the nurse tech in the room (step 370) can be automatically detected using any number of basic personnel tracking systems know in the art, for example, infrared ID badges and receivers, or the nurse tech could enter information into a workstation. Each task remains open until closed by the designated and assigned role. For example, if the task is for a nurse, the task will not be closed if maintenance personnel enter the room.

Once the nurse tech's presence is detected in the patient room (step 370), the system may identify the nurse tech as "busy" 375 and the patient as "busy" 380. Once the nurse tech completes the task 385 (which in this case may need to be manually entered into the system), the task, the responder, and the time is logged by the system for tracking and analysis 390. The nurse tech is then available to receive a new Task 395. Every action may be automatically documented and stored for instant or future evaluation.

In the example set forth in FIG. 5, only a subset of the rules that may be executed is depicted. For example, for a bath request order, other rules (not depicted) may also be executed. For example, a nurse workstation may be notified that a bath request has been entered, patient status updated, escalation timers set, physicians notified, etc.

Staffers that are currently assigned to tasks can also be tracked so that tasks can be efficiently allocated. For example, if a first patient request was assigned to Nurse #1, and Nurse #1 has not completed the task, a second patient request may be communicated to Nurse #2. This same allocation can be made for all types of communications to all different types of staffers, for example, personnel in housekeeping, maintenance, janitorial, and dietary. Allocation can also be made for equipment.

Not depicted in FIG. 5, but running through most Tasks, is the associated time targets and escalation procedures. Tasks may contain time targets, which age and selectively "remind" page if the system does not see a specific caregiver role present where an open request exist.

In the example depicted in FIG. 5, steps 360, 365, 370, 375, 380, 385, and 390 all preferably operate in the order intializer 65 and object VM 70 in a LUA (, or other interpretive language, solution space. In this context, the order intializer 65 analyzes exactly what needs to happen to properly execute the rules specified by the scheduler 40.

Figure 6:
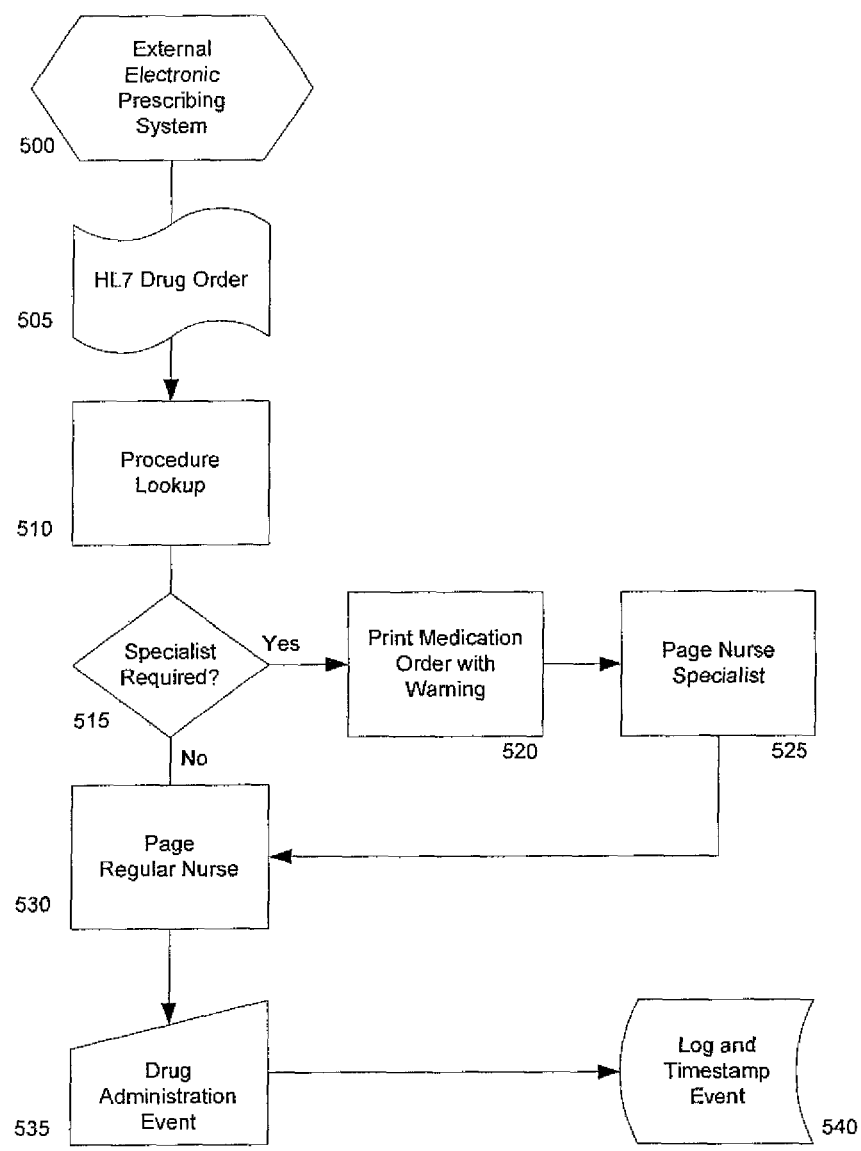
FIG. 6 illustrates another exemplary embodiment of task creation and completion.

Another exemplary workflow example of one embodiment of the invention is depicted in FIG. 6. FIG. 6 depicts execution of rules triggered by input from an external system. Referring to FIG. 6, in step 500, a user logs on to a workstation having an external electronic prescribing system (i.e., an application binding 25). In this example, a user may input a HL7 drug order (step 505). The order is passed to the rules engine 20 for procedure lookup (step 510). In step 515, the drug ordered is checked to determine whether a black box warning is associated with the medication, i.e., whether the FDA has determined that the medication may have some serious adverse side effects. If so, in step 520, the medication order is printed with the associated warning. A nurse specialist may also be contacted (step 525) to assist in the administration of this type of medication. In this example, if the medication does not have a black box warning, a regular nurse will be contacted (step 530). In step 535, the drug is administered to the patient, either by a regular nurse (if no black box warning) or by a nurse specialist (if a black box warning does exist). After administration, the event is logged (step 540).

Figure 7:
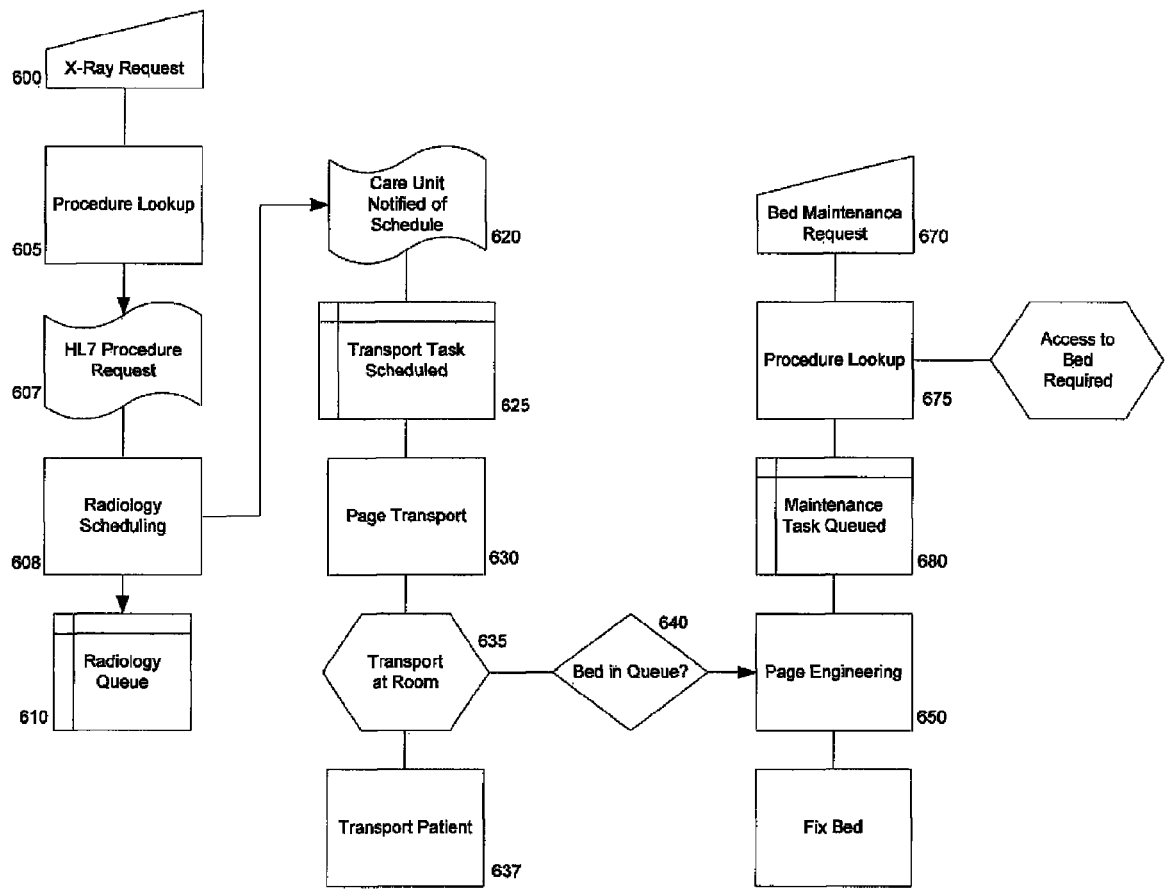
FIG. 7 illustrates another exemplary embodiment of task creation and completion.

Another exemplary workflow example of one embodiment of the invention is depicted in FIG. 7. In FIG. 7, there are two rules that are being executed, an X-ray request and a bed maintenance request. In this context, a facility may only want to perform maintenance on a particular bed when there is no patient in it. Thus, FIG. 7 depicts an exemplary workflow how the system will coordinate workflow in this manner.

In FIG. 7, in step 670, there is a bed maintenance request. The request could be automatically triggered (for example, preventative maintenance every 6 months), or could be as a result of a manual input (for example, a nurse noticing that part of the bed frame was not secure). The bed maintenance request is passed to the rules engine 20 for procedure lookup (step 675), which indicates, in this example, that the bed must be available for maintenance, i.e., no patient in it. At that point, the maintenance task can be queued (step 680).

Still referring to FIG. 7, perhaps running parallel to the bed maintenance request, is an X-ray request (step 600). In step 605, the order procedure is looked up in the rules engine 20. For this example, the patient may be expected to be "busy" for 1 hour plus the transport time. In step 607, an HL7 procedure request is made to radiology, and in step 608, the X-ray request coordinated with radiology scheduling, and in step 610, a radiology request in put in the queue. In step 620, radiology is notified of the schedule for the X-ray. In step 625, a transport task is queued. A transport clerk can then be paged (step 630), and the transport clerk reports to the patient room (step 635). As the transport clerk transports the patient for the X-ray (step 637), the bed is now available, and can be placed in the queue (step 640). At this point, a page may be sent to engineering 650 to have the maintenance performed on the bed.

An alternative embodiment of the present invention provides for intelligent routing of calls to remote patient response centers and particular operators located at the remote patient response center. The intelligent routing may be handled by a patient call master station or other similar facilities. The principle of selecting among call centers may be based on rules associated with individual patient information, and with fault tolerance mechanisms that ensure there is always a well-defined place that answers patient calls. The routing of the call may be based on various factors, for example, the load of calls at each individual remote patient response center, the likely language preference of the caller, necessary skills of the operator, availability of individual operators, or call allocation during peak call times. For example, if one remote patient response center is overloaded with patient calls, the system can automatically route the call to a different remote patient response center that is not at capacity. Moreover, the system can route calls from a specific geographic location to a remote patient response center that is more likely to have a dispatcher/responder that speaks the language of the caller, i.e., skills-based routing. Skills-based routing also can cover areas of domain knowledge. Certain dispatchers/responders may be trained in communications with pediatric patients, and such calls will preferentially be routed to them.

Once the call is received at the remote patient response center, the remote patient response center computer network carry communications to the appropriate dispatcher/responder. For example, the local system will monitor the dispatchers/responders, and the first priority may be to find an available dispatcher/responder.

The present invention may be utilized with a number of basic services and clinical services provided by the facility. Examples of basic services that can be implemented using the present invention include patient transport, package management, food services, facility maintenance, and bed management, although others could be implemented as well. Examples of clinical services include laboratory dispatch, pharmacy requests, and respiratory orders, although others could be implemented as well.

Patient Transport

In the present invention, rather than having nurses seek and find wheelchairs and transport patients, a transport request can be input into a workstation (or automatically generated), and a task generated for and automatically communicated to a non-clinical person designated to respond to that task. The entire event is tracked and documented from transport request to completion. The system can track elapsed time and escalate tasks if necessary. The system can also communicate directly to housekeeping, nursing, and/or admissions. For example, if a patient transport is for discharge, a task for housekeeping to clean the room could automatically be generated, and a notification to admissions that the room is now available. All results can be reported.

One advantage of the present invention includes the automatic association of patient information with the request. For example, if a request to transport John Doe in Room 421 is made, the system can automatically associate the fact that John Doe weighs 400 pounds and will need a "big boy" wheelchair.

Package Management

In the present invention, rather than having a third party courier service or the employee needing delivery handling the package, a courier service request can be input into a workstation (or automatically generated), and a task generated for and automatically communicated to a non-clinical, designated person to respond to that task. The entire event is tracked and documented from transport request to completion. The system can track elapsed time and escalate tasks if necessary. Reporting formats can include time from order to completion, target exemption, STAT courier by personnel, courier by cost center, courier by transaction number, courier by package type, and courier summary.

Food Service

In the present invention, a diet order in can be entered into a workstation (or automatically generated), and a task generated for and automatically communicated to food service. For example, a dietary aide may receive a page for a meal tray and verify the diet order on the workstation. The dietary aide writes the meal ticket and delivers the ticket to the tray line for delivery. The dietary aid may close the task on the local workstation. In this example, a new task may be generated for someone to deliver the tray. The entire event is tracked and documented from request to completion. The system can track elapsed time and escalate tasks if necessary.

Facility Maintenance

In the present invention, users can enter facility work orders into a workstation, and a task generated for and automatically communicated to a technician. The tech can proceed to the particular area in the facility to which the request was directed and receive details from the local workstation, or he/she can obtain the work order from a workstation in the maintenance department. The entire event is tracked and documented from work order request to completion. The system can track elapsed time and escalate tasks if necessary.

The facility maintenance application can also track equipment inventory via the ID badges on the equipment. Their presence can be detected using the receivers. Moreover, the rules engine 20 and database 15 can automatically track and generate work orders for preventative maintenance on various equipment based on the equipment information associated with the ID badge. The application also allows for basic asset tracking of the facility inventory.

Bed Management

In the present invention, enterprise wide bed status may be managed jointly from admissions and housekeeping, while keeping staff informed of their status via workstations. When a patient is discharged or a transport request for discharge is documented, a task may be generated for and automatically communicated to housekeeping to clean the room. The housekeeping tech can clean the room and complete the task via a workstation in the particular area of the facility in which they were working or in housekeeping's main office. The "clean" status of the room is recorded in the database 15 and the room available to admitting when a request for a bed is received. The entire event is tracked and documented from task request to completion. The system can track elapsed time and escalate tasks if necessary.

Another advantage is the ability to reserve bed availability and integrate the bed management functionality with local and regional emergency operations. Thus, in the event of a mass casualty situation, through an interface with the facility's admissions/discharge application, emergency personnel will have access to bed availability at the facility, and may reserve beds in advance of patient arrival.

Laboratory Dispatch

In the present invention, rather than paging or calling a Lab Tech with a verbal order, a nurse can enter a Lab request via a workstation. The Lab Tech assigned to that specific Lab request is automatically text paged. Thus, a task is generated for and automatically communicated to the appropriate person to respond to that task. The information is also communicated to the workstation in the Lab. The entire event is tracked and documented from lab request to completion, including a history of recent orders and activity by bed. The system can track elapsed time and escalate tasks if necessary. Examples of reporting can include order time/page time, collect time, received in lab time, person paged first, person paged second, etc.

Pharmacy

In the present invention, rather than paging or calling the pharmacy, a nurse can enter a pharmacy request via a workstation. The appropriate pharmacy personnel is automatically text paged. Thus, a task is generated for and automatically communicated to the appropriate person to respond to that task. The information is also communicated to the workstation in the pharmacy. The entire event is tracked and documented from pharmacy request to completion, including a history of recent orders and activity by bed. The system can track elapsed time and escalate tasks if necessary.

Respiratory Orders

The present invention can also receive, store, and communicate respiratory orders. As new orders are entered into a workstation, they are transmitted to the assigned respiratory therapist by text pager and available via a workstation. Respiratory therapists can receive those orders that pertain to their assigned beds. The workstations allow for printing of current and completed respiratory orders, assignments and text pages that have been dispatched. On unique feature is that previous bed locations can be displayed while viewing orders in the current location of the patient.

Although a preferred embodiment of the invention has been described using specific terms and devices, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of various other embodiments may be interchanged both in whole or in part. Therefore, the spirit and scope of the appended claims should not be limited to the description of the preferred version contained herein. Moreover, while the preferred embodiment has been described primarily with respect to a healthcare facility, those of skill in the art will readily recognize that the communication and workflow management system and method is readily useable in other facilities. The rules and communication methods are simply adapted to the needs of a particular organization.

What is claimed is:

1. A system for managing workflow of a healthcare facility, comprising:
   (a) a computer network, comprising at least two computers, that receives an invocation condition over a healthcare facility information network, said invocation condition having one or more associated task requests, wherein said invocation condition is triggered by a monitored medical device reaching a pre-determined monitored medical device reading threshold;
   (b) where the computer network identifies a plurality of staffers, each having associated qualifications to respond to one or more task requests, a physical location and a workload, wherein information about the qualifications, physical location and workload of said staffers is stored in a database located in an electronically readable media within the computer network;
   (c) where the computer network automatically associates patient information with the one or more task requests, and where the patient information comprises a patient name, a room number, a monitored medical device reading, and a summary of relevant patient allergic condition, wherein the patient information is stored in a database comprising a transactional database and a federated data model, and where the federated data model stores current processes and data, and where the federated data model purges historical data;
   (d) where the computer network assigns one or more primary staffers to complete the task request, wherein the primary staffers assigned to the task request are determined at least in part by the qualifications, physical location and workload of the primary staffers;
   (e) where the computer network communicates the task request to the assigned primary staffers;
   (f) where the computer network assigns a primary escalation timer value based at least in part on the nature of the task request and starts the primary escalation timer;
   (g) where the computer network tracks progress towards completion of the task request;
   (h) where the computer network escalates the task request if the task request is not completed by the end of the primary escalation timer by notifying one or more secondary staffers of the uncompleted task request and a secondary escalation timer value is assigned and started as part of such notification;
   (i) where the computer network further escalates the task request by notifying one or more tertiary staffers of the uncompleted task request if the task request is not completed by the end of the secondary escalation timer;

(j) where the computer network repeats step (i) until the task request is completed; and (k) where the computer network documents the completion of the task request by storing the documentation in an electronically readable media within the computer network.

2. The system of claim 1, where the task request comprises a patient request.

3. The system of claim 1, where the task request comprises a housekeeping request.

4. The system of claim 1, where the task request comprises a dietary request.

5. The system of claim 1, where the system monitors staffer locations with an asset tracking system.

6. The system of claim 1, where escalation of the task request comprises a reminder message to the same qualified staffers originally notified of the task request.

7. The system of claim 1, where escalation of the task request comprises notification of supervisory personnel.

8. The system of claim 1, where documenting the completion of the task request stored electronically in said database for later analysis.

9. The system of claim 1, where the workflow of the healthcare facility is managed from a geographically remote patient response center.

10. A method for managing workflow of a healthcare facility comprising:

(a) storing, by a computer network comprising at least two computers, patient data and staffer data in a database comprising a transactional database and a federated data model, said staffer data comprising qualifications to respond to a plurality of tasks, physical location and workload associated with a plurality of staffers wherein the federated data model stores current processes and data and purges historical data;

(b) storing, by the computer network, a plurality of tasks in a rules engine, said rules engine in communication with said database and in communication with one or more application bindings;

(c) automatically associating, by the computer network, the patient data with the task request, and where the patient data comprises a patient name, a room number, a monitored medical device reading, and a summary of relevant patient allergic conditions;

(d) receiving, by the computer network, in the rules engine from an application binding an invocation condition associated with one or more of said tasks, where the invocation condition is triggered by a monitored medical device reaching a pre-determined threshold;

(e) assigning, by the computer network, one or more qualified primary staffers to said task based on said qualifications, physical location and workload of the primary staffers;

(f) communicating, by the computer network, said task to one or more qualified primary staffers;

(g) monitoring, by the computer network, if the task is completed by the primary staffer in a first predefined amount of time;

(h) escalating, by the computer network, the task by notifying one or more qualified secondary staffers of the uncompleted task if the task is not completed by the end of the first predefined amount of time and monitoring if the task request is completed by the one or more secondary staffers within a second predefined amount of time;

(i) further escalating, by the computer network, the task by notifying one or more qualified tertiary staffers of the uncompleted task if the task is not completed within the second predefined amount of time and repeating this step (h) until the task is completed;

(j) documenting, by the computer network, the completion of the task request by storing the documentation in an electronically readable media within the computer network.

11. The method of claim 10, where the secondary staffers of (h) are selected based on at least qualifications and other active tasks assigned to the secondary staffers.

* * * * *